United States Patent
Hommann et al.

(10) Patent No.: US 6,960,194 B2
(45) Date of Patent: Nov. 1, 2005

(54) NEEDLE PROTECTION DEVICE FOR AN INJECTION UNIT

(75) Inventors: Edgar Hommann, Grossaffoltern (CH); Peter Hostettler, Ersigen (CH)

(73) Assignee: TecPharma Licensing AG, Burgdorf (CH)

( * ) Notice: Subject to any disclaimer, the term of this patent is extended or adjusted under 35 U.S.C. 154(b) by 244 days.

(21) Appl. No.: 10/233,315

(22) Filed: Aug. 29, 2002

(65) Prior Publication Data

US 2003/0040725 A1 Feb. 27, 2003

Related U.S. Application Data

(63) Continuation of application No. PCT/CH01/00113, filed on Feb. 22, 2001.

(30) Foreign Application Priority Data

Mar. 1, 2000 (DE) .......................... 100 09 816

(51) Int. Cl.⁷ ............................. A61M 5/32; A61M 5/00
(52) U.S. Cl. ....................................... 604/198; 604/263
(58) Field of Search ................................ 604/263, 192, 604/197, 198, 164.08

(56) References Cited

U.S. PATENT DOCUMENTS

| | | |
|---|---|---|
| 4,787,891 A | 11/1988 | Levine et al. |
| 4,915,702 A | 4/1990 | Haber |
| 5,201,720 A | 4/1993 | Borgia et al. |
| 5,242,416 A | 9/1993 | Hutson |
| 5,304,137 A | 4/1994 | Fluke |
| 5,360,408 A | 11/1994 | Vaillancourt |
| 5,498,244 A | 3/1996 | Eck |
| 5,609,577 A | 3/1997 | Haber et al. |
| 5,976,111 A * | 11/1999 | Hart ........................... 604/198 |

* cited by examiner

*Primary Examiner*—Michael J. Hayes
(74) *Attorney, Agent, or Firm*—Dorsey & Whitney LLP

(57) ABSTRACT

A needle protecting device including a base body, a needle protecting sleeve mounted on the base body, wherein in a protective position the sleeve surrounds an injection needle and in a second position exposes the injection needle, a first block and a second block, one connected to the needle protecting sleeve and the other connected to the base body, wherein in the protective position of the sleeve the blocks engage to prevent the sleeve from moving into the second position, and a safety-release for releasing the engagement of the blocks.

19 Claims, 3 Drawing Sheets

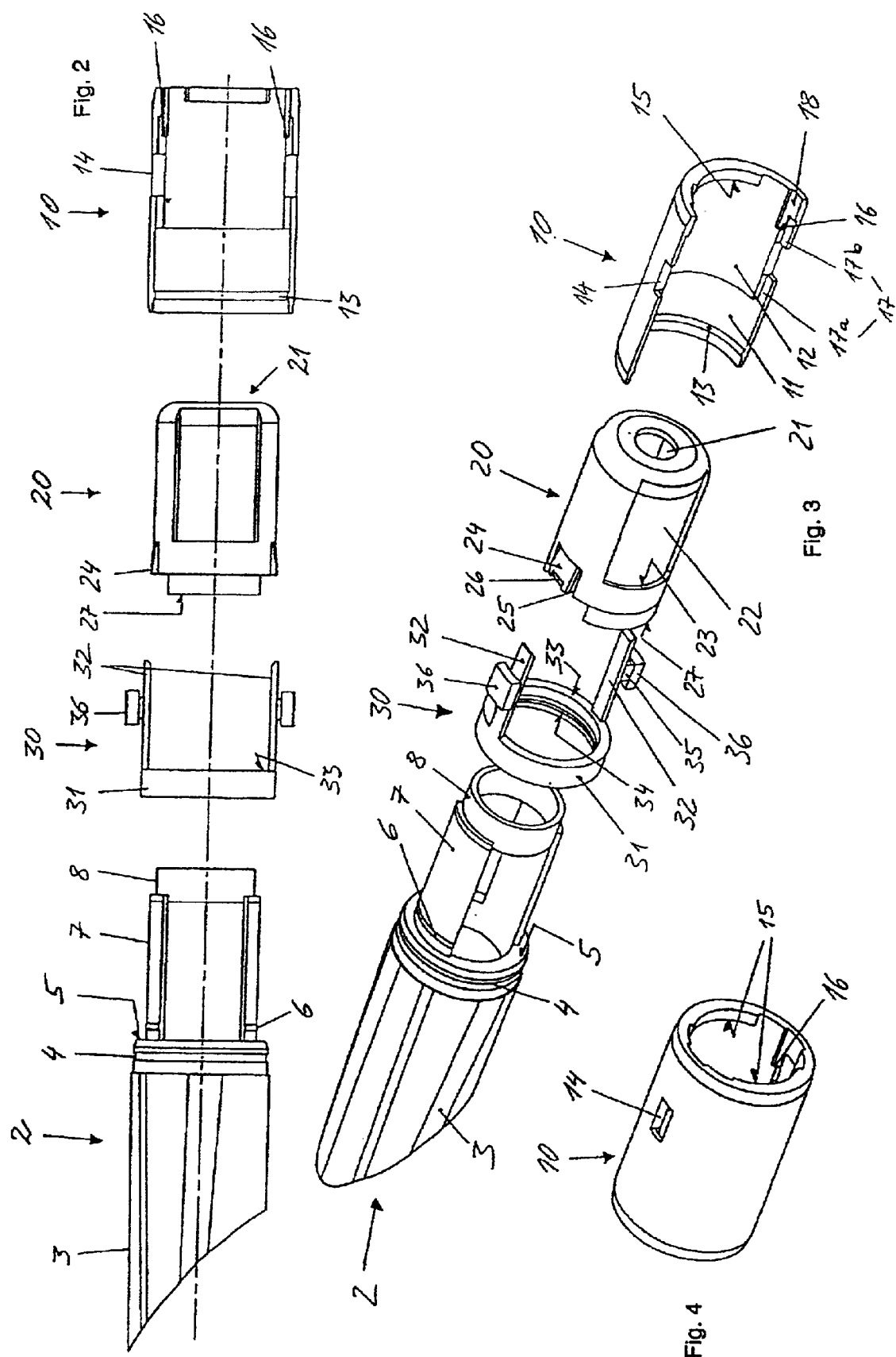

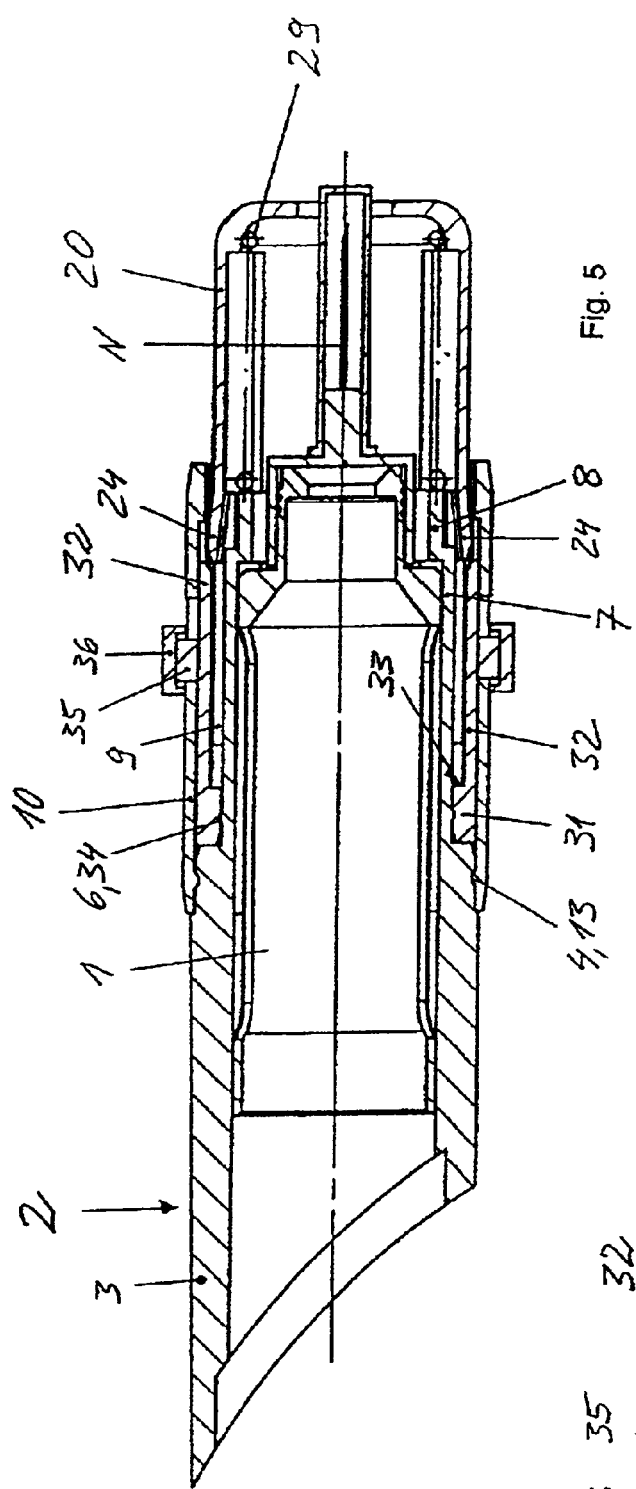
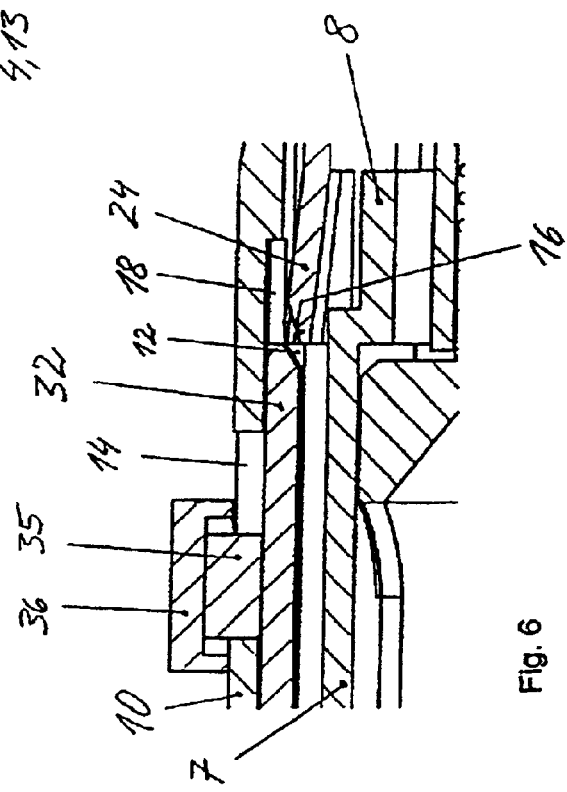

NEEDLE PROTECTION DEVICE FOR AN INJECTION UNIT

PRIORITY CLAIM

This is a Continuation Application of International Application No. PCT/CH01/00113, filed on Feb. 22, 2001, which claims priority to German Application No. DE 100 09 816.9, filed on Mar. 1, 2000, both of which are incorporated herein by reference.

BACKGROUND

The invention relates to needle protecting devices for injection devices. It also relates to methods of making and assembling a needle protecting device, and to methods of using a needle protection device and an injection device equipped with a needle protection device. In one embodiment, while in a protective position, the needle holder in accordance with the present invention surrounds the injection needle of an injection device and prevents the needle from being unintentionally exposed.

An injection device comprising a needle protecting device is known from U.S. Pat. No. 5,609,577. An injection needle is surrounded by a needle protecting sleeve. The needle protecting sleeve is mounted, axially slidably, on a casing of the injection device. In the protective position, the needle protecting sleeve is secured by a block against the injection needle being unintentionally slid or exposed. Once the block is released, the needle protecting sleeve can be slid into a rear position in which the injection needle protrudes freely beyond the retracted needle protecting sleeve. When the needle protecting sleeve is retracted, a tension spring of the needle protecting device is tensed. If the needle protecting sleeve is relaxed after the injection, then the needle protecting sleeve pre-latches back into its protective position under the tension stress of the tension spring. The blocking mesh or connection is automatically re-established in the protective position.

The block is formed by a cam and a guideway for the cam. The guideway consists of one section extending axially, and another section connected to it at a right angle. In the protective position, the cam meshes with the angled section of the guideway. In this way, the needle protecting sleeve is prevented from sliding and exposing the injection needle. For releasing the block, the needle protecting sleeve is rotated relative to the base body until the cam comes to rest in the axially extending section of the guideway. In this rotational position, the needle protecting sleeve can be slid relative to the base body, into the rear position. The tension spring does not only serve to pre-tension the needle protecting sleeve into the front position. Simultaneously, it also tenses the needle protecting sleeve into the rotational position in which the cam abuts in the angled section of the guideway. Thus, for injecting, the needle protecting sleeve is first rotated against the force of the tension spring and then, likewise against the force of the tension spring, slid into its rear position.

In the known needle protecting device of the '577 patent, the tension spring is a substantial element of the block. By using a spring to secure the needle protecting sleeve in its protective position, a complicated construction is required for the blocking mechanism. Furthermore, the normal functioning of the blocking mechanism is substantially dependent on the spring. The spring can for instance break or jam. If the spring malfunctions, it cannot be guaranteed that the needle protecting sleeve is securely blocked.

SUMMARY

It is an object of the invention to provide a needle protecting device for an injection device, which in a protective position securely blocks a needle protecting sleeve against sliding, and which is not susceptible to faults. Preferably, a blocking mechanism should require a minimal number of movable parts, and be designed simply.

In one embodiment, the present invention provides a needle protecting device for an injection device comprising a sleeve-shaped base body, a needle protecting sleeve operably coupled to the base body, wherein, in a protective position, the needle protecting sleeve surrounds an injection needle of the injection device and, in a second position, exposes the injection needle, a first block and a second block, one of which is immovably connected to the needle protecting sleeve and the other of which is immovably connected to the base body, wherein, in the protective position of the needle protecting sleeve, a blocking mesh is formed by the blocks pushing axially against each other, the blocking mesh preventing the needle protecting sleeve from sliding into the second position, and a safety-release for the blocking mesh, wherein the first block is formed by a bendable latch connected substantially rigidly to one of the needle protecting sleeve and base body and wherein the blocking mesh is released by bending the latch.

In one embodiment, a needle protecting device in accordance with the present invention comprises a sleeve-shaped base body and a needle protecting sleeve. An injection needle of the injection device protrudes beyond a front end of the base body. The needle protecting sleeve is mounted, axially slidably, on the base body. In a protective position, the needle protecting sleeve surrounds the injection needle. Once it has been axially slid into a rear position, the needle protecting sleeve exposes the injection needle. In the protective position, the needle protecting sleeve is blocked against retracting relative to the base body and the injection needle. In the protective position of the needle protecting sleeve, a blocking mesh (i.e., engagement, joint, connection, etc.) exists between a first blocking means and a second blocking means, in that the two blocking means push against each other axially. One of the blocking means is connected non-sliding to the needle protecting sleeve and the other blocking means is connected non-sliding to the base body. The blocking mesh thus prevents the needle protecting sleeve from sliding from the protective position to the rear position. Lastly, the needle protecting device comprises a safety-release means for releasing the blocking mesh between the first blocking means and the second blocking means.

In accordance with the invention, the first blocking means is formed by an elastically bendable latch which is rigidly connected to the needle protecting sleeve or the base body. In the protective position of the needle protecting sleeve, the latch abuts the second blocking means, which forms a latch stopper, in the axial direction. The blocking mesh of the blocking means is released by bending the latch. The latch is bent out of blocking mesh (i.e., engagement, connection, etc.) with the latch stopper. By being bent, the latch is elastically tensed, i.e., a restoring force is generated in the latch. The latch is preferably fully relaxed in its blocking position, which it assumes in the protective position of the needle protecting sleeve.

For securely blocking, the needle protecting device in accordance with the invention requires only the elastically bendable latch and the latch stopper. A third element, for example in the form of the tension spring known from the prior art, is not required. The number of parts required for manufacturing the block is reduced. The latch in accordance with the invention combines the blocking function of the known cam and the restraining and/or securing function of the known spring.

In one embodiment, the second blocking means is formed on a surface area of the base body or of the needle protecting sleeve. The blocking means is a wall, which protrudes in a radial direction or exactly radially out from the surface area or into the surface area. The surface area can be an inner surface area or an outer surface area of the base body or an inner surface area or an outer surface area of the needle protecting sleeve. In one embodiment, the wall forming the second blocking means is formed on an inner surface area of the base body. The second blocking means can be formed by a single wall or also by a number of walls, in particular as described above.

In another embodiment, the safety-release means is mounted on the base body, slideably movable relative to the needle protecting sleeve. A sliding mount is formed such that the safety-release means slides along the latch when moved and so presses on the latch in such a direction that the latch is bent out of its blocking mesh (i.e., engagement, connection, etc.) The pressure on the latch acts perpendicular to the direction in which the safety-release means is moved. The safety-release means can, however, also be formed like a push-button or other suitable mechanism which pushes against the latch in the direction in which the push-button itself moves relative to the base body. Although the safety-release means can also form the latch stopper itself, and in this case is itself moved out of the blocking mesh when released, a separate latch stopper is provided which is connected to the needle protecting sleeve or the base body, axially non-sliding. In one embodiment, the latch stopper lies next to sliding path of the safety-release means. It is a stopper which is rigidly connected to the base body.

A needle protecting device comprising a safety-release means moveably arranged relative to the needle protecting sleeve exhibits the advantage that the needle protecting sleeve itself does not have to be operated in order to release the blocking mesh of the blocking means. Thus, a user no longer has to then pay attention to the release of the blocking mesh when the needle protecting sleeve is already pressed against the skin for the injection, as is the case when using the needle protecting sleeve of U.S. Pat. No. 5,609,577. Releasing the blocking mesh and retracting the needle protecting sleeve can be separated from each other by the movably arranged safety-release means. Furthermore, the blocking mesh can be released and re-established any number of times, while the needle protecting sleeve remains in the protective position. It is not necessary for an injection to be performed once the blocking mesh is released in order to restore the blocked protective position.

In one embodiment, the safety-release means is secured in the protective position of the needle protecting sleeve such that it is not slaved by the needle protecting sleeve when the needle protecting sleeve moves into its protective position. In this way, the safety-release means is advantageously also secured against being unintentionally moved, for example due to vibrations. The safety-release means is secured by a locking mesh between the safety-release means and the base body in the protective position of the needle protecting sleeve. Correspondingly, the base body is provided with a first locking mesh means, and the safety-release means with a second locking mesh means. The locking mesh can be released.

In one embodiment, the needle protecting device is formed such that after an injection, the needle protecting sleeve advances again into the protective position and the blocking mesh of the latch and the latch stopper in accordance with the invention is automatically established in the protective position. The needle protecting device allows repeated injections, wherein the blocking mechanism automatically blocks the needle protecting sleeve in its protective position against being unintentionally retracted. When it is retracted into the rear position, the needle protecting sleeve slaves the safety-release means as far as a position in which the safety-release means locks with the base body. By forming the locking mesh so that it can be released, it is possible to operate the needle protecting device repeatedly. In principle, however, it would also be possible to design the locking mesh of the safety-release means to be non-releasable. In the case of a non-releasable locking mesh, a needle protecting device comprising a latch, which automatically pre-latches into the blocking stopper, could only be used for an injection if it is ensured that the blocking mesh of the latch cannot be released in any way other than by the safety-release means. The safety-release means is preferably slaved by the needle protecting sleeve pressing loosely against the safety-release means when the needle protecting sleeve is retracted.

In one embodiment, the latch is formed as an axially extending latch finger comprising a front-facing abutting area. It is formed as one piece together with the base body, or as one piece together with the needle protecting sleeve. In another embodiment, the latch could also project in a radial direction from the base body or the needle protecting sleeve.

The blocking mechanism of the needle protecting sleeve can comprise a number of latches, for forming a number of blocking meshes with corresponding blocking stoppers. A number of safety-release means, i.e., at least one for each latch, can be arranged non-sliding relative to each other on a common base, such that by appropriately operating the base, all the blocking meshes can be released simultaneously. The number of safety-release means can, however, also be mounted and operable independently of each other, in order for example to even more securely prevent the blocking meshes from being unintentionally released.

In one embodiment, the blocking mechanism is surrounded by a sleeve portion of the base body, such that only the safety-release means can be accessed from without. The sleeve portion of the base body in question fulfils the function of a covering sleeve. The needle protecting sleeve is pushed into the covering sleeve when sliding into the rear position, but in that position can still protrude some way beyond the covering sleeve.

In another embodiment, a cam projects from the safety-release means and through an opening of the covering sleeve, and the safety-release means is slidable along the covering sleeve. The cam is supported on the outer surface of the covering sleeve, which prevents a radially inward directed pressure being exerted on the safety-release means when it is operated. The forces acting when the safety-release means is operated are thus collected by the covering sleeve.

The base body can be formed as one or a number of parts. When the base body is formed as a number of parts, said number of parts are connected to each other, axially non-sliding. The base body can be formed by the casing of the injection device, as is the case in the needle protecting device of U.S. Pat. No. 5,609,577. In another embodiment, the needle protecting device is formed as an independent device whose base body is adapted to a casing of an injection device, such that the base body may be connected, non-sliding, to the casing of the injection device. Such a needle protecting device, which may be independently handled, comprises a base body, which is simply pushed onto the casing of the injection device and fixed non-sliding to the casing. It is advantageous to form a plug-on sleeve which is very simply plugged onto an existing injection device, up against a stopper, and then fixed to the casing of the injection device in a positive and frictional lock. By appropriately adapting the shape of its base body, the independent needle protecting device can advantageously serve for retro-fitting existing injection devices which allow injection even without a needle protecting device.

BRIEF DESCRIPTION OF THE DRAWINGS

FIG. 2 is a longitudinal section of the components of the needle protecting device of FIG. 1;

FIG. 3 is a perspective representation of the components of FIG. 2;

FIG. 4 depicts the covering sleeve of the needle protecting device according to FIGS. 1 to 3;

FIG. 5 is a longitudinal section of the needle protecting device according to FIGS. 1 to 4 in its assembled state; and FIG. 6 is a detail from FIG. 5.

DETAILED DESCRIPTION

Figure 1:
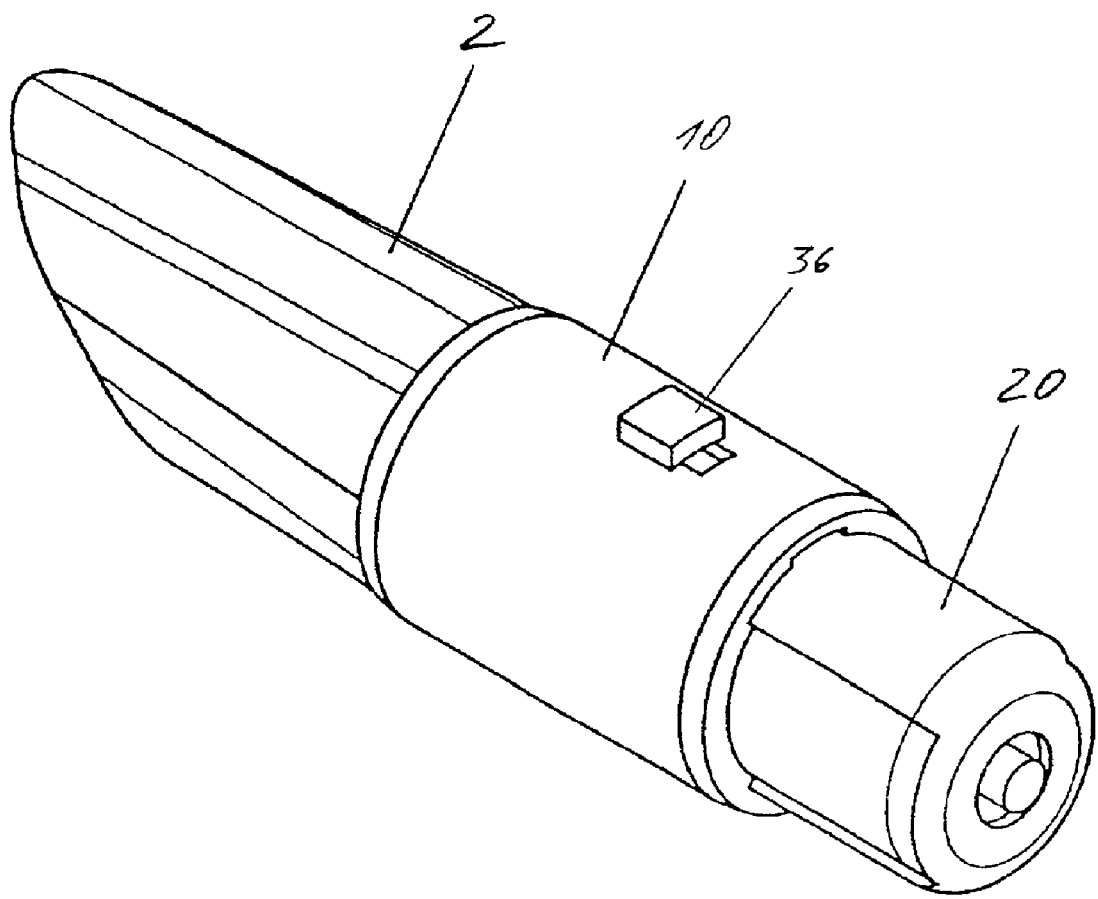
FIG. 1 depicts a needle protecting device.

FIG. 1 shows a needle protecting device in its assembled state. A plug-on sleeve 2, a covering sleeve 10 and a needle protecting sleeve 20 in a co-axial arrangement may be recognized. The covering sleeve 10 is latched onto the plug-on sleeve 2. The latching connection can practically no longer be released. When assembled, the plug-on sleeve 2 and the covering sleeve 10 can be regarded as a single base body 2, 10. No sliding movements are possible, in particular between the plug-on sleeve 2 and the covering sleeve 10. The needle protecting device may be plugged Onto an injection device for administering a product fluid, in particular a medicinal fluid, for example insulin. To this end, the plug-on sleeve 2 is formed adapted to the injection device in question.

The needle protecting sleeve can be slid back and forth in the axial direction within the covering sleeve 10. In FIG. 1, it assumes a protective position. In the protective position, the needle protecting sleeve 20 is extended up to a stopper formed within the covering sleeve 10 and surrounds an injection needle of the injection device up to and beyond a tip of the needle. In the protective position, the needle protecting sleeve 20 protects the user from injuries from the injection needle. At the same time, the injection needle is protected from being damaged. In the protective position, the needle protecting sleeve 20 furthermore forms a blind, such that the user cannot see the injection needle. In particular, this reduces the inhibition threshold to be observed in users who inject the product themselves.

In the protective position, the needle protecting sleeve 20 is blocked against sliding into the covering sleeve 10. This blocking prevents the needle protecting sleeve 20 from being unintentionally retracted and the injection needle exposed. Directly before an injection, the user has to release the block on the needle protecting sleeve 20, i.e., he has to release the safety on the needle protecting sleeve 20. This is done by axially sliding an operating element 36. Once the block is released, the needle protecting sleeve 20 can be retracted, against an elastic restoring force relative to the plug-on sleeve 2 and the covering sleeve 10, into a rear position. In the rear position, the needle protecting sleeve 20 exposes the injection needle. The needle protecting sleeve is retracted in the course of insertion during the injection. If the injection needle is withdrawn again out of the tissue after the injection, the needle protecting sleeve 20 is advanced again by the elastic restoring force. As soon as the needle protecting sleeve 20 has reached its protective position again, it is automatically re-blocked. The block can be repeatedly released.

FIGS. 2, 3 and 4 show the components of the needle protecting device individually, before being assembled. The needle protecting device is formed by five components, namely the plug-on sleeve 2, the covering sleeve 10, the needle protecting sleeve 20, a safety-release means 30 and a restoring element in the form of a pressure spring 29, which however is only shown in FIG. 5. In one embodiment, however, once these five components have been assembled, the operating element 36 still has to be connected to the safety-release means 30. The four components 2, 10, 20 and 30 and also the operating element 36 are each embodied in one piece as plastic injection parts.

The plug-on sleeve 2 comprises a whole, first sleeve region 3 and a second sleeve region comprising two sleeve segments 7 and a ring 8. The two sleeve segments 7 project from a facing area of the first sleeve region 3, offset by 180°. The two sleeve segments 7 are distanced from each other at their ends by the ring 8 and thus the second sleeve region is reinforced. In a transition region between the first sleeve region 3 and the sleeve segments 7, a recess or groove 4 is formed circumferentially. Lastly, the two sleeve segments 7 each comprise a tangentially extending swelling or bulge 6 near their ends on their outer surface areas.

The covering sleeve 10 comprises a surface area which is broken only by two opposing openings 14. In the vicinity of the end of the covering sleeve 10, a swelling or bulge 13 runs around the inner surface area. In the assembled state, the bulge 13 comes to rest in the groove 4 of the plug-on sleeve 2. At the other end of the covering sleeve 10, two collar segments 15 project radially inwards. The two collar segments 15 serve as front stoppers and as linear guides for the needle protecting sleeve 20.

On the inner surface area of the covering sleeve 10, two stoppers 16 are formed in a symmetrical arrangement and offset by 180° with respect to each other. The stoppers 16 are each formed by a pair of areas facing the end of the covering sleeve 10 and pointing radially to the inner surface area of the covering sleeve 10. Viewed in the axial direction, the stoppers 16 are arranged between the openings 14 and the collar segments 15. Furthermore, two straight, axially extending channels 17 are formed in the inner surface of the covering sleeve 10. Each one of the openings 14 extends through one of the channels 17 and sub-divides the respective channel into a first channel section 17a and a second channel section 17b. The stoppers 16 directly border the second channel section 17a of each of the channels 17 and thus each form one edge of the channel edging. One inner surface region 11 of the covering sleeve 10 is extended toward another inner surface region 12. The transition is formed by a circumferential collar interrupted by the channels 17.

The needle protecting sleeve 20 exhibits the shape of a cap, by forming a base at its rear end, said base being broken only by a central opening 21 for the injection needle. Two latches 24, axially free, project from a facing area of the needle protecting sleeve 20 in a symmetrical arrangement and offset by 180°. The latches 24 each radially protrude slightly beyond an outer surface area of the needle protecting sleeve 20. The latches 24 are each formed in an exposed notch 25 of the surface area of the needle protecting sleeve 20. In one embodiment, the latches 24 are each laminate. In one embodiment they are rectangular laminae. In another embodiment, the latches are a single layer. At their rear ends, the latches 24 are tapered or angled in a central region 26 on their outward pointing upper sides. The latches 24 are elastic in the radial direction around their foot regions.

Lastly, the needle protecting sleeve 20 comprises a recessed face region 22 on its outer surface area, said face region 22 tapering off towards the end of the needle protecting sleeve 20 and forming a collar 23 to the rest of the outer surface area at one end. Another recessed face region 22 is formed in the same way on the diametrically opposing side of the needle protecting sleeve 20.

The safety-release means 30 is formed by a ring 31 and two tongues 32 projecting axially from the ring 31 and arranged symmetrically, offset by 180° with respect to each other. A recess or groove 34 runs around the inner surface area of the ring 31. A cam 35 projects outwards from each of the outward pointing surfaces of the tongues 32. An operating element 36 is attached to each of the cams 35. In one embodiment, the operating elements 36 are only attached to the cam 35 after the four components 2, 10, 20, 30 have been assembled.

When assembling the device, the needle protecting sleeve 20 is first pushed into the covering sleeve 10. The two collar segments 15 together with the recesses 22 form a linear guide for the needle protecting sleeve 20. The co-operation between the collar segments 15 and the two recesses 22 simultaneously ensures that as soon as it is inserted, the needle protecting sleeve 20 assumes a rotational position relative to the covering sleeve 10 such that the latches 24 are aligned with the stoppers 16. Due to their radially projecting length in the inner surface region 12 of the covering sleeve 10, the latches 24 are bent radially inwards against their own elastic restoring forces. As soon as the latches 24 have been pushed over the stoppers 16, they pre-latch radially outwards again due to their own elastic restoring forces, such that their facing areas then oppose the stoppers 16, directly facing them. In this blocking mesh (i.e., engagement, connection, etc.) of the latches 24, it is no longer possible to retract the needle protecting sleeve 20 relative to the covering sleeve 10. The latches 24 then lie in front of the stoppers 16 in an enlargement 18 of the channel section 17b of the covering sleeve 10. More precisely, only the edge regions of the latches 24 remaining to the left and right of the angled central region 26 push against the stoppers 16 in the blocking mesh. If the needle protecting sleeve 20 is advanced slightly further, then the collars 23 push against the collar segments 15. The co-operation between the collar segments 15 and the collars 23 is principally intended to prevent the needle protecting sleeve 20 from being able to fall forwards out of the covering sleeve 10. The latches 24 are, however, still accessible from without, from the facing side of the covering sleeve 10 using a pointed tool.

In the next assembly step, the safety-release means 30, in the rotational position relative to the other components as shown in FIG. 3, is likewise pushed into the covering sleeve 10, behind the needle protecting sleeve 20. As it is inserted, the tongues 32 are guided tightly and laterally into the channels 17. Insertion is complete when the cams 35 reach the region of the openings 14 and the tongues 32 are therefore able to pre-latch outwards.

The operating elements 36 are then adhered to the cams 35 or securely attached in some other way. The operating elements 36 are shaped such that they press against the outer surface area of the covering sleeve 10 and so keep any radial pressure during operation off the tongues 32. The operating elements 36 thus also simultaneously serve to support the safety-release means 30 and/or the tongues 32 on the covering sleeve 10. The operating elements 36 can also be formed as one piece on the cams 35, for example mushroom-shaped. In such an embodiment, they would be placed against the respective cam once they have been passed through the openings 14 and once passed through would elastically expand, in particular shore up, to achieve the support.

Before the covering sleeve 10 is connected to the plug-on sleeve 2, the pressure spring 29 (FIG. 5) is inserted into the pre-assembled needle protecting sleeve 20 as far as the base of the needle protecting sleeve 20.

In a last assembly step, the covering sleeve 10, comprising the components 20 and 30 and the pressure spring 29, is pushed onto the plug-on sleeve 2 until the bulge 13 is locked into the groove 4. Since the covering sleeve 10 is not broken in the region of the bulge 13, and due to a sufficient rigidity overall, the locking connection between the groove 4 and the bulge 13 cannot be released again, at least not without tools or without destroying it.

If the safety-release means 30 does not yet assume the locking position shown in FIG. 5, then the needle protecting sleeve 20 can be retracted into its rear position, for example within the context of functional testing by the manufacturer. The needle protecting sleeve 20 presses the safety-release means 30 into the rear locking position such as the safety-release means 30 assumes in the representation in FIG. 5. The safety-release means 30 is slaved by the needle protecting sleeve 20 pressing with a facing side 27 against a facing side 33 of the safety-release means 30 facing towards it. The two bulges 6 meshing with the groove 34 of the safety-release means 30 establishes a releasable locking connection. The locking connection is nonetheless sufficiently firm to prevent it being released due to the vibrations, jerking and the like which commonly occur during use.

The function of the needle protecting device is best seen from FIGS. 5 and 6. FIG. 5 shows the needle protecting device completely assembled and attached to an injection device (not shown). The plug-on sleeve 2 surrounds an ampoule holder 1. The ampoule holder 1 is sleeve-shaped and accommodates an ampoule which is filled with a medicine fluid. The ampoule holder 1 is inserted into the plug-on sleeve 2 up to the ring 8. The segments 7 (FIG. 3) allow the ampoule holder 1 to be viewed. An injection needle 40 connected in the usual way to an outlet of the ampoule protrudes beyond the ends of the plug-on sleeve 2 and of the covering sleeve 10. In the representation in FIG. 5, the needle protecting sleeve 20 assumes its protective position, in which it protectively surrounds the injection needle 40 over its entire length. The latches 24 oppose their respective stopper 16, facing them axially, i.e., they abut their respective stopper 16. The safety-release means 30 assumes its locking position, in which there is no mesh (i.e., engagement, connection, etc.) between the tongues 32 and the latches 24. The needle protecting sleeve 20 is thus blocked against retracting.

An annular space 9 is formed between the sleeve segments 7 and the covering sleeve 10, into which space the needle protecting sleeve 20 can be slid up to its position if the blocking mesh between the latches 24 and the stoppers 16 has been released beforehand. This is released by sliding the safety-release means 30.

In the following, the functional sequence in an injection will be described, wherein reference is to be made at all times to all the figures.

Once a protective cap still surrounding the injection needle 40 has been removed, a first injection can be performed.

Directly before the injection, the user pushes the safety-release means 30 in a releasing direction by means of the operating elements 36. In the course of sliding the safety-release means 30, each of the tongues 32 slides over the latch 24 assigned to it. Since the latches 24 protrude outwards beyond the sliding contact areas of the tongues 32 facing them, the latches 24 are pressed radially inwards when the tongues 32 slide past the latches 24 with their sliding contact areas. The safety-release means 30 is advanced as far as an end position, wherein the latches 24 are bent away from the stoppers 16, such that the needle protecting sleeve 20 can be pushed into the annular space 9, the latches 24 pressing elastically against the tongues 32. The tongues 32 are as wide as the tapered or angled central regions 26 (FIG. 3) of the latches 24. The tongues 32 are likewise tapered towards their facing areas. Tapering the latches 24 or the tongues 32 or both particularly securely prevents self-locking which could impede sliding over the latches 24.

Once the block on the needle protecting sleeve 20 has been released, the injection device is placed on the skin, such that the needle protecting sleeve 20 lies on the skin via its base and the injection needle 40 points to the surface of the skin approximately perpendicularly. In this injecting position, the needle protecting sleeve 20 is slid into the annular space 9 as far as a rear position by the pressure of the injection device against the surface of the skin. Simultaneously, the injection needle 40 pierces the skin and penetrates into the tissue below.

As the needle protecting sleeve 20 is slid into the annular ring 9, a facing area 27 (FIG. 2) of the needle protecting sleeve 20 meshes with the facing area 33 of the safety-release means 30. The mesh consists of a loose abutting of the two facing areas 27 and 33. In this way, the needle protecting sleeve 20 presses the safety-release means 30 into the locking position shown in FIG. 5, in which the two bulges 6 mesh with the recess 34. If, after the injection, the injection needle is withdrawn from the tissue again and the needle protecting device is relaxed, then the needle protecting sleeve 20 slides back in the needle-protecting direction due to the force from the pressure spring 29. As the needle protecting sleeve 20 is moved, the safety-release means 30 remains in its locking position. As soon as the needle protecting sleeve 20 has been advanced far enough that the latches 24 pass in front of the stoppers 16, the latches 24 latch back radially outwards due to the restoring forces generated in them by being bent away, such that they again oppose the stoppers 16 and the blocking mesh is re-established.

The injection device can be disposed of together with the needle protecting sleeve in its blocked protective position. Even in the case of repeated injections, the needle protecting device likewise fulfills its protective function. Lastly, the needle protecting device can also be used in combination with a number of injection devices in succession. In principle, it can even be used with various injection devices in an embodiment as a plug-on device, if the plug-on sleeve 2 is adapted in its shape to the respective injection device. For the majority of injection devices, it can be assumed that the ampoules exhibit approximately the same cross-sections, such that it is only actually necessary to adapt the plug-on sleeve 2.

In the foregoing description, embodiments of the invention have been presented for the purpose of illustration and description. It is not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

What is claimed is:

1. A needle protecting device for an injection device, said needle protecting device comprising:
    a) a sleeve-shaped base body;
    b) a needle protecting sleeve which is mounted, axially slidably, on said base body;
    c) wherein, in a protective position, said needle protecting sleeve surrounds an injection needle of said injection device and, in a second position, exposes said injection needle;
    d) a first blocking means and a second blocking means, of which one is connected non-sliding to said needle protecting sleeve and the other is connected non-sliding to said base body;
    e) wherein, in said protective position of said needle protecting sleeve, a blocking mesh is formed by said blocking means pushing axially against each other and so preventing said needle protecting sleeve from sliding into said second position;
    f) and a safety-release means for releasing said blocking mesh, wherein
    g) said first blocking means is formed by an elastically bendable latch which is connected rigidly to said needle protecting sleeve or said base body;
    h) and in that said blocking mesh of said blocking means is released by bending said latch against a restoring force generated in said latch by bending it.

2. The needle protecting device as set forth in claim 1, wherein the base body is connected, non-sliding, to a casing of the injection device.

3. The needle protecting device as set forth in claim 1, wherein the base body is formed by a casing of the injection device.

4. The needle protecting device as set forth in claim 1, wherein said safety-release means is mounted on said base body, movable relative to said needle protecting sleeve.

5. The needle protecting device as set forth in claim 1, wherein said safety-release means is mounted on said needle protecting sleeve, movable relative to said base body.

6. The needle protecting device as set forth in claim 1, wherein said safety-release means is mounted on said base body, slidable relative to said needle protecting sleeve, in such a way that when moved, it slides along said first blocking means and bends said first blocking means out of said blocking mesh.

7. The needle protecting device as set forth in claim 1, wherein a locking mesh exists between said safety-release means and said base body in said protective position of said needle protecting sleeve, which secures said safety-release means against being slaved by said needle protecting sleeve moving to said protective position.

8. The needle protecting device as set forth in claim 7, wherein said locking mesh of said safety-release means can be released.

9. The needle protecting device as set forth in claim 1, wherein said needle protecting sleeve slaves said safety-release means as it slides into said second position, until said safety-release means enters into a locking mesh with said base body.

10. The needle protecting device as set forth in claim 9, wherein said locking mesh of said safety-release means can be released.

11. The needle protecting device as set forth in claim 1, wherein said needle protecting sleeve presses loosely against said safety-release means and slaves said safety-release means as it slides into said second position.

12. The needle protecting device as set forth in claim 1, wherein said first blocking means projects axially from said needle protecting sleeve or said base body, may be bent radially, and in said protective position of said needle protecting sleeve is bent out of said blocking mesh, against its elastic restoring force.

13. The needle protecting device as set forth in claim 1, wherein said second blocking means is formed on a surface area of said base body or of said needle protecting sleeve.

14. The needle protecting device as set forth in claim 1, wherein said safety-release means pushes over said first blocking means and bends radially inwards, to release said blocking mesh.

15. The needle protecting device as set forth in claim 1, wherein:

said base body comprises a covering sleeve into which said needle protecting sleeve can be moved;

said covering sleeve comprises an opening; and a cam of said safety-release means protrudes through said opening.

16. The needle protecting device as set forth in claim 15, wherein said cam is supported on an outer surface area of said covering sleeve against a movement directed radially inwards.

17. The needle protecting device as set forth in claim 1, wherein:

said base body comprises an inner sleeve region and a covering sleeve which surrounds said inner sleeve region;

an annular space remains between said inner sleeve region and said covering sleeve; and said needle protecting sleeve may be slid into said annular space.

18. The needle protecting device as set forth in claim 1, wherein a restoring element is supported on said base body and said needle protecting sleeve, said restoring element being tensed when said needle protecting sleeve is slid into said second position and advances said needle protecting sleeve out of said second position into said protective position.

19. The needle protecting device as set forth in claim 1, wherein said base body may be plugged onto a casing of an injection device.

* * * * *